United States Patent [19]

Bosker

[11] Patent Number: 4,516,937
[45] Date of Patent: May 14, 1985

[54] SYSTEM FOR DENTURE SUPPORT USING A TRANSMANDIBULAR IMPLANT

[76] Inventor: Hans Bosker, Essen 14, 9751 NC Haren, Netherlands

[21] Appl. No.: 556,520

[22] Filed: Nov. 30, 1983

[51] Int. Cl.³ .............................................. A61C 8/00
[52] U.S. Cl. .................................................... 433/173
[58] Field of Search ............... 433/173, 174, 175, 176

[56] References Cited

U.S. PATENT DOCUMENTS 3,748,739  7/1973  Thibert .............................. 433/176

FOREIGN PATENT DOCUMENTS 882466  7/1961  Fed. Rep. of Germany ...... 433/173
770696  5/1954  United Kingdom ................ 433/174

Primary Examiner—Robert Peshock
Attorney, Agent, or Firm—Sperry, Zoda & Kane

[57] ABSTRACT

A system providing support on the lower jaw for a submaxillary denture wherein a base plate comprising an arcuate metal strip having an intermediate portion, the centerline of which in plan view being an arc across a subtending chord 34 mm in length and with a height of 8 or 10 mm;

a bridging means comprising hooking means for coupling means included in a submaxillary denture;

a set of posts to stand on said intermediate portion for carrying said bridging means;

a fixing means for each of said posts to fix said bridging means; and a set of cortical screws to adjoin said base plate fixedly to the lower face of the lower jaw at locations on either side of each of said posts.

Each of its parts is made up of gold 18-5 (gold of 18 carat, allowed with 5% platinum).

Auxiliary means for mounting said base plate and said posts in a lower jaw comprise a jig for drilling and tapping and a concurrent alignment means, said jig being unilaterally a replica of the face of the base plate turned to the interface with the lower jaw.

15 Claims, 12 Drawing Figures

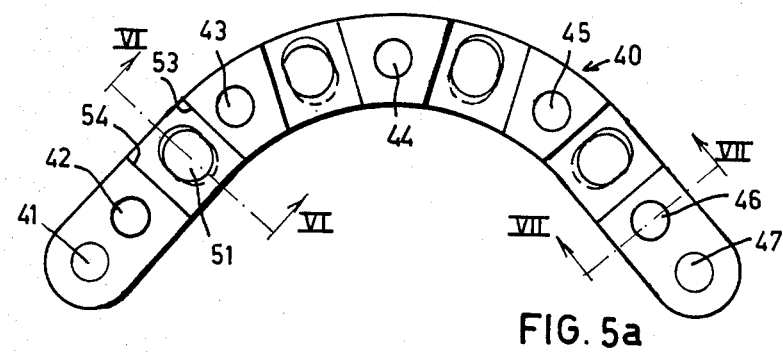
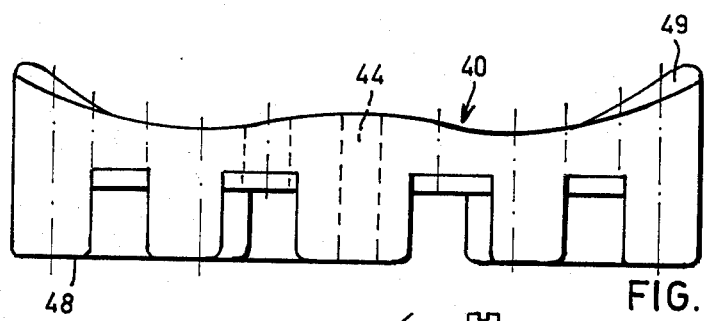
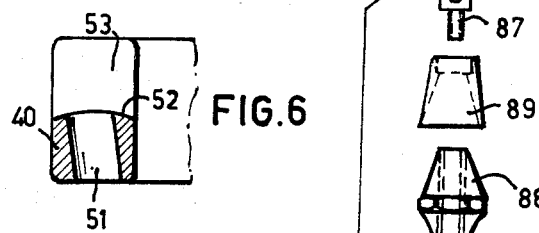
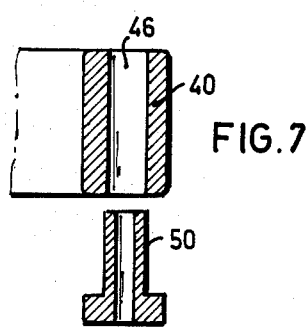
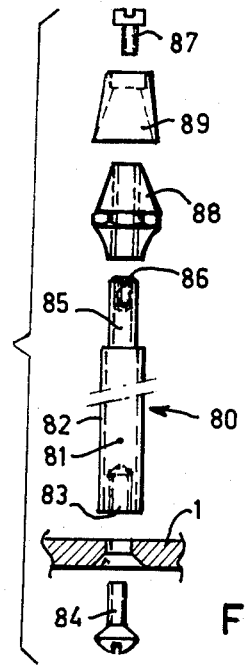

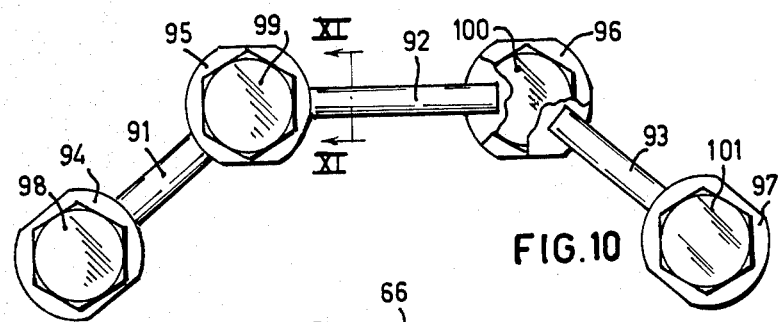
FIG.10
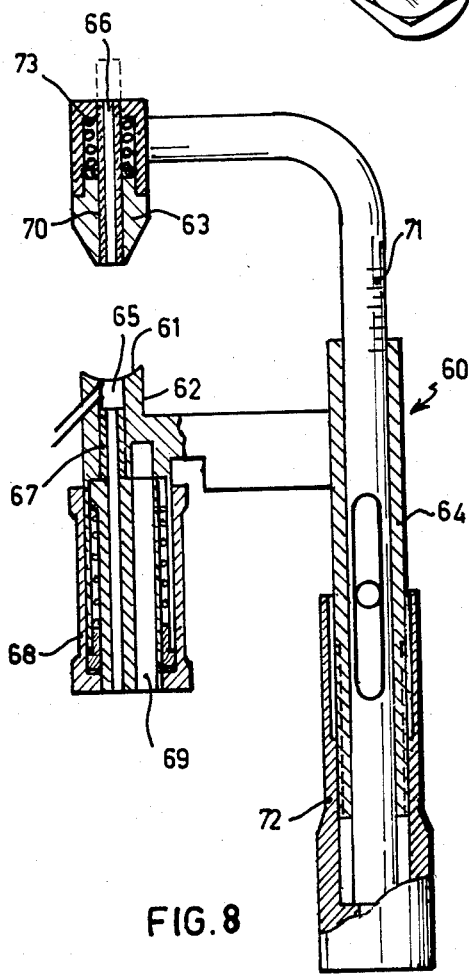
FIG.11
FIG.8

SYSTEM FOR DENTURE SUPPORT USING A TRANSMANDIBULAR IMPLANT

The invention relates to a system providing support on the lower jaw for a submaxillary denture.

A similar system, examples of which are not known to applicant, can be considered as a solution to the problem that a submaxillary denture frequently requires adjustment to the shape of the upper face of the lower jaw, as said shape is changing due to resorption of the body of the lower jaw bone. Such resorption is among other things caused by the stress exerted by the denture upon the bone tissue, in particular so during biting and chewing. Other than with a maxillary denture loading the hard palate as well, this stress cannot be distributed over any hard tissues apart from the lower jaw bone itself. When exceeding a critical value an elevated stress exerted upon bone tissue tends to resorption of bone tissue. Apparently said critical value of the exerted stress is easily exceeded under the specified conditions.

The present solution to the above problem is based on the understanding that no resorption of bone tissue occurs by exerting thereupon tensile force by way of its periosteum. To the contrary the bone tissue is actually prompted to increase.

The system according to the invention brings about a reduction of the exerted stress to a value below the critical by at least partly converting the forces when chewing and biting, into a tensile force exerted by the periosteum.

According to the present invention the said system is characterized by a base plate comprising an arcuate metal strip having an intermediate portion, the centerline of which in plan view being an arc across a subtending chord 34 mm in length and with a height of 8 or 10 mm;

a bridging means comprising hooking means for coupling means included in a submaxillary denture;

a set of posts to stand on said intermediate portion for carrying said bridging means;

a fixing means for each of said posts to fix said bridging means; and a set of cortical screws to adjoin said base plate fixedly to the lower face of the lower jaw at locations on either side of said posts.

It is remarkable that the dimensions found for the base plate which is indispensable in the system, can be well defined. The arc having a height of 8 mm across a chord of 34 mm in length defines a base plate for an adult male person and the arc having a height of 10 mm across a chord of 34 mm in length defines a base plate for an adult female person.

The posts reduce the stress exerted on the bone by partly transferring said stress to the cortical screws resulting in a tensile force upon the periosteum which is returned across the base plate at the lower face of the lower jaw.

Preferably the said set of posts comprises four posts, each having external thread to fix the post in the lower jaw bone, internal thread at its base end for connecting the base plate by means of a screw and an external thread at its head end for said fixing means.

In this preferred embodiment the external thread provided in each post to fix same in the lower jaw bone transfers a portion of the exerted stress directly to the bone tissue, however, exerting a stress below the critical value. The other portion of the exerted stress is converted into a tensile force through the periosteum through the sufficiently rigid base plate.

Advantageously the base plate, the posts, the cortical screws and the bridging means are made up of a gold/platinum alloy 18-5 (18 carat gold with 5% platinum). This material combines mechanical strength with ductility and is compatible with the various tissue and body fluids with which the system in situ gets into contact.

In the preferred embodiment the system according to the invention comprises some simple auxiliaries to be used to advantage when setting the base plate, the posts and the bridging means in the lower jaw bone.

The features of said auxiliaries and in general of some variations of the system according to the invention will now be stated in a specification of a number of embodiments of the invention, said specification referring to drawings, wherein FIG. 1 shows an isometric view of an assembly according to a first embodiment;

FIGS. 5a and 5b show a plan view and an elevation respectively of a jig comprised in the system according to the invention;

FIG. 6 shows a cross-section of the jig according to FIGS. 5a and 5b;

FIG. 7 shows another cross-section of the jig according to FIGS. 5a and 5b;

FIG. 8 shows an elevation, partially in cross-section of an alignment means according to the invention;

FIG. 9 shows a post in the assembly according to FIG. 1;

FIG. 10 shows a preferred embodiment of the bridging means comprised in the assembly according to the invention; and FIG. 11 shows a cross-section of a preferred embodiment of a beam comprised in the bridging means.

Figure 1:
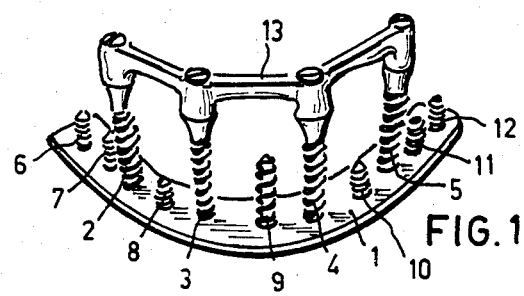

FIG. 1 is a drawing derived from a photograph and shows a view of the assembly according to a first preferred embodiment comprising the base plate 1, four post screws 2, 3, 4 and 5 and seven cortical screws 6 up to and including 12, and the assembled bridging means 13 such as the assembly would look, when mounted in the lower jaw. The drawing is somewhat larger than actual size.

Figure 2:
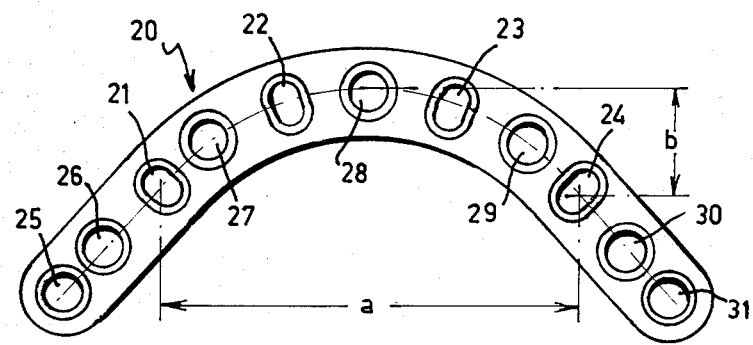
FIG. 2 shows a plan view of a base plate comprised in an assembly according to the invention.

In FIG. 2 a base plate for an adult male person is drawn in plan view about twice as large as actual size. The four locations each for fixing a post are centered on the centerline of the gold alloy 18-5 strip 20 forming the base plate. In between the extreme locations for a post the centerline forms an arc across a chord a of 34 mm in length with a height b of 8 mm. For fixing the posts elongated apertures 21 through 24 are arranged at the locations to secure same, the longitudinal directions of said apertures pointing to the center of said arc. Each of the elongated apertures 21 through 24 is to receive a screw to fix the post onto the base plate. Around each aperture a bevel is made in the material of the base plate 20 in order to deal with an oblique position of the post, if any, with respect to the base plate using a screw head adapted to the bevel.

Furthermore the base plate comprises circular apertures 25 through 31 for receiving cortical screws to adjoin the base plate to the lower face of the lower jaw bone, directly behind the chin ("cortical" refers to the hard rind of the lower jaw bone having a spongy core). The borders of these circular apertures are also bevelled, so that the screw head can at least partly be sunk into the body of the base plate. These circular apertures, seven in number, are arranged at either side of the apertures 21 through 24 for securing a post. The apertures 27, 28 and 29 are centered on the described arc. The apertures 25, 26 and 30, 31 are respectively arranged in one of two wing portions of the base plate, their centerline being tangent to the arc.

Figure 3:
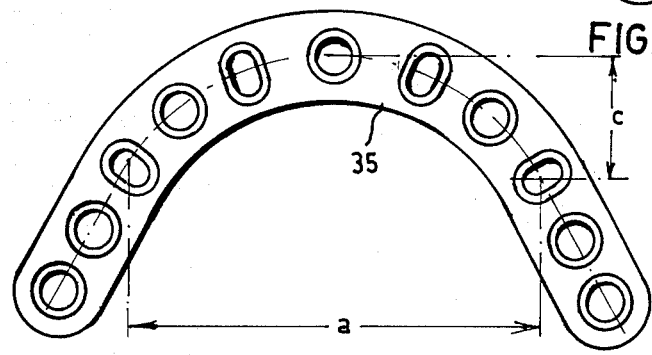
FIG. 3 shows a plan view of another base plate.

FIG. 3 shows a base plate 35 in the embodiment for adult female persons. The arrangement is similar to the arrangement of the base plate 20 shown in FIG. 2 provided the height c of the arc across the chord a is 10 mm in length.

Figure 4:
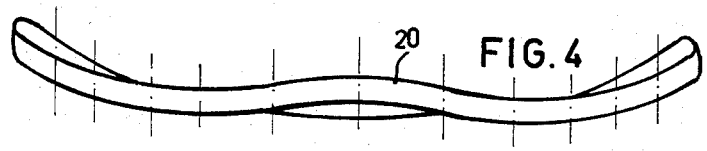
FIG. 4 shows an elevation of the base plate according to FIG. 2.

FIG. 4 shows the base plate according to FIG. 2 in a view perpendicular to the view in FIG. 2. The plane of base plate 20 is symmetrically curved to adapt the shape of the lower face of the lower jaw bone.

Just as a result of the curved shape the posts will always stand in a somewhat oblique position with respect to the base plate. The shape indicated in FIG. 4 is a standard shape which is the same for all adult male persons. The shape of the base plate for adult female persons is also a standard shape.

FIGS. 5a and 5b respectively show a plan view and an elevation of the convex side of a jig 40 for drilling and tapping being an auxiliary when mounting the assembly of the base plate, the posts and the cortical screws in the lower jaw bone. Through the openings arranged in the jig 40 concurrent with the apertures in the base plate, apertures for the cortical screws are drilled and tapped up from below. Therefor the jig 40 is provided with through holes 41 up to and including 47 upright from the flat entry face 48 of the body of jig. 40. The exit face 49 of the jig 40 is formed as a replica of the face of the base plate 20 to be adjoined to the lower jaw bone. This means that two jigs are needed, one for males and one for females.

The apertures 41 through 47 for preparing the mounting of the cortical screws have a diameter corresponding with that of the tap. For guiding a drill, spacing means 50 can be inserted into the tap-guiding apertures 41 through 47. Such a spacing means 50 is shown in FIG. 7 being a cross-section along the lines VII—VII in FIG. 5a. The inner diameter of spacing means 50 corresponds with the outer diameter of the drill to be used. The aperture in spacing means 50, the actual drilling jig, has for example a diameter of 2 mm and the aperture 46 in the body of the jig 40 has a diameter of 3 mm, which are appropriate sizes for shank and thread of cortical screws respectively.

The application of through holes in the lower jaw bone for the posts can be done at an oblique angle with the entry face 48 of the jig 40. Therefor the jig 40 provides guiding faces for an alignment device as described hereafter. The corresponding apertures in the jig have an elongated cross-section and their axes are in an oblique direction with respect to the entry face.

The latter is represented in the cross-section of the jig, centrally through the aperture 51 as shown in FIG. 6. In this cross-section the body of jig 40 has a recessed upper face 52 being a portion of a cylinder surface. The recess is situated in between two parallel guiding faces 53 and 54. These guiding faces are directed along the longitudinal axes of the elongated cross-section of the apertures in the jig 40, such as the aperture 51.

FIG. 8 shows the alignment means 60 with the concave supporting face 61 that is a counter means of an upper face such as the upper face 52 which supporting face thus fits the recessed upper faces in the jig 40. The supporting face 61 is the tooling face of the anvil 62 of the two-piece alignment means 60 embodied as a sliding gauge. Laterally the anvil 62 fits in the recesses in the jig 40 in between the guiding faces 53 and 54 forr example to enable swinging said alignment means about a longitudinal axis of the jig 40 that is to say an axis parallel to the tangent of the arc according to which the jig 40 is shaped, to wit in the center of an aperture, such as aperture 51. The anvil 62 is therefor provided with flat cheecks, both intersecting the cylindrical tooling face 61 at right angles.

Opposite the anvil 62 in the alignment means 60 a pin 63 is slidably arranged in a sleeve 64 secured to the anvil 62. Both the anvil 62 and the pin 63 are provided with a through hole 65 and 66 respectively, said through holes being coaxial, each having a diameter corresponding with the outer diameter of the tap for a post in the form of a screw.

To make through hole 65 in anvil 62 suitable for a drill, a bushing 67 can be inserted therein, said bushing 67 advantageously being a tool in a revolving tool box 68 having as a further bore a through hole 69 with the diameter of the through hole 65, thus with the outer diameter of the tap.

In pin 63 a bushing 70 is comprised which is movable in opposition to bias of a spring 73, bushing 70 having the same inner diameter as bushing 67 in anvil 62.

On pin 63 a scale 71 is present to enable the alignment means to serve as a sliding gauge for measuring the elevation of the lower jaw bone. This measure of elevation is of importance for the lengths to be selected of the posts being eventually located in threaded apertures which have been drilled through the lower jaw bone by means of the alignment means. Pin 63 is movable in sleeve 64 by means of an adjustment device 72.

FIG. 9 shows an exploded view of an embodiment of post 80 such as shown assembled in FIG. 1. In the shank of a post screw 81 with external thread 82 an internally threaded aperture for a connecting screw 84 is arranged at its base to be connected with the base plate 1 (FIG. 1). The head end 85 of the shank of post scew 81 is threaded having in its top face a recess 86 with internal thread adapted to a terminal screw 87. The length of the threaded head end 85 is sufficient to accomodate a two-piece collar comprising two collar pieces 88, 89 to be placed successively on the head end of the post, the collar piece to be arranged firstly having an internal thread fitting the external thread of the head end of the post, the collar piece to be arranged secondly on the head end of the post being secured by the locking screw 87. The upper collar piece 89 of the collar to be placed secondly is an element of the bridging means 13 (FIG. 1). One or two bridges are soldered to the upper collar piece 89 after determining their size in situ.

The lower collar piece 88 is made up with a conical top face and an internal thread fitting the head end thread 85. The upper collar piece 89 is made up with a recess concurrent with the conical top face of the lower collar piece 88. Thus the upper collar piece can be temporarily left out, to wit for constructing the bridging means after measuring the respective bridge sizes without having the respective screw ends forming the same number of inconvenient obstacles in the oral cavity. The inconvenience is prevented by the body of the lower collar piece which extends up to the top face of the threaded end.

In FIG. 3 a preferred embodiment of the bridging means is shown. In this embodiment the bridging means can be mounted directly on the posts. The ends of beam pieces 91, 92, 93 are received in notches in the lower collar piece and are locked therein by the upper collar pieces 94, 95, 96, 97 respectively. Finally the collar is secured with terminal locking screws 98, 99, 100, 101 respectively.

The beam pieces 91, 92, 93, 94 preferably have drop shapes in cross-section and are cut to size and arranged in one movement with the surgical operation in which the posts and the base plate are set. The beam pieces are hooking means for coupling means included in a submaxillary denture.

Each post having such a length that the bridging means is situated freely in the oral cavity in order to enable engagement of a submaxillary denture. The drop shape of the perpendicular cross-section of the beam pieces (FIG. 11) is precisely selected in view of said engagement.

In a variation of the preferred embodiment widenings are provided at the beam piece ends which are received in concurrent recesses at the ends of the notches in the lower collar piece.

Preferably all the parts of the support system are made up of 18-5 gold that is 18 carat gold alloyed with 5% platinum. This alloy is compatible with body-tissue and body fluids and has the desired characteristics as to ductility and strength.

The support system according to the invention permits standardisation to a high degree. The time needed for arranging the parts of the support system in the lower jaw bone can be limited as a result. This is of great importance, quite a significant surgical operation being at issue. The only parts to be present in various length sizes are the posrt screws and the long cortical screws to be placed between said post screws.

I claim:

1. An apparatus providing support on the lower jaw for a submaxillary denture characterized by a base plate comprising an arcuate metal strip having an intermediate portion, the centerline of which in plan view bring an arc across a subtending chord approximately 34 mm in length and with a height of approximately 8 to 10 mm; a bridging means comprising hooking means for coupling means included in a submaxillary denture;
   a set of posts to stand on said intermediate portion for carrying said bridging means;
   a fixing means for each of said posts to fix said bridging means; and a set of cortical screws to adjoin said base plate fixedly to the lower face of the lower jaw at locations on either side of each of said posts.

2. Apparatus according to claim 1, characterized in that the said set of posts comprises four posts, each having external thread to fix the post in the lower jaw bone, internal thread at its base end for connecting the base plate by means of a screw and an external thread at its head end for said fixing means.

3. Apparatus according to claim 2, characterized in that each of said fixing means comprises a two-piece collar, said collar pieces being sequentially arranged at the head end of the post, the collar piece to be arranged firstly having an internal thread to fit the said external thread at the head end of a post, and a terminal screw to fix the collar piece to be arranged secondly.

4. Apparatus according to claim 3, characterized in that the said collar piece to be arranged secondly when assembled, is part of said bridging means being made up of four of said collar pieces and three connecting beam pieces forming the said hooking means by means of soldering or welding.

5. Apparatus according to claim 4, characterized in that the upper face of said collar piece to be arranged firstly and in accordance with its position in said bridging means has either one or two notches both to receive a clean end of a beam piece forming a hooking means, the said collar piece to be arranged secondly serving as a locking means to lock one or two of the beam pieces in said notch or notches respectively.

6. Apparatus according to claim 5, characterized in that notches are made in said collar piece to be arranged secondly in concurrence with notches in the collar piece to be arranged firstly.

7. Apparatus according to claim 5, characterized in that said notches are recessed inwards to receive a concurrent widening of said beam piece end.

8. Apparatus according to claim 5, characterized in that said collar piece to be arranged secondly comprises internal thread to fit the external thread at the head end of a post, thus forming the said terminal screw.

9. Apparatus according to claim 1, characterized in that said beam pieces in perpendicular cross-section are drop shaped to cooperate with a spring terminal, said spring terminal being fixed in the body of a submaxillary denture.

10. Apparatus according to claim 1, characterized in that each of its parts is made up of gold 18-5 (gold of 18 carat, allowed with 5% platinum).

11. Apparatus according to claim 1, characterized in that auxiliary means for mounting said base plate and said posts in a lower jaw comprise a jig for drilling and tapping and a concurrent alignment means, said jig being unilaterally a replica of the face of the base plate turned to the interface with the lower jig, the jig being provided with apertures in its height direction to guide a tapping means when tapping thread in previously drilled holes in the lower jaw in conformity with the respective locations of the cortical screws at the base plate, and with guiding faces on either side of a through-hole in conformity with the respective locations of the posts at the base plate, and a means to enable swing of said alignment means on a longitudinal axis of said jig in cooperating with a counter means of said alignment means, further comprising apertured inserts for guidance of a drilling jig in tap guiding aperture and said alignment means additionally comprising cheeks which maintain said alignment means, when correctly positioned, in lateral conjunction in between said guiding faces in said jig and in superposition above said through-hole and said through-holes between said guiding faces for said alignment means having an elongated cross-section, the longitudinal direction of which being in accordance with the swing of said alignment means.

12. Apparatus according to claim 11, characterized in that said alignment means comprises a drilling jig and a tapping jig being combined in a revolving tool box, said revolving tool box being translatably contained in a brace having an adjustable width and being opposite a drill guiding means.

13. Apparatus according to claim 12, characterized in that said drill guiding means comprises a bushing being movable in opposition to spring bias in a box at an end of said brace, said bushing having an outer diameter similar to the tap outer diameter.

14. Apparatus according to claim 12, characterized in that said brace carries a scale to display the width of the brace in between said revolving tool box and said box of the drill guiding means.

15. Apparatus according to claim 12, characterized in that said counter means in the alignment means is coupled to the arm of said brace which comprises the revolving tool box carrying arm.

* * * * *

UNITED STATES PATENT AND TRADEMARK OFFICE
CERTIFICATE OF CORRECTION

PATENT NO. : 4,516,937
DATED : May 14, 1985
INVENTOR(S) : Hans Bosker

It is certified that error appears in the above-identified patent and that said Letters Patent are hereby corrected as shown below:

Claim 11, line 39, change the first occurrence of the word "jig" to -- jaw --.

Claim 11, line 48, change "cooperating" to -- cooperation --.

Signed and Sealed this

Eighth Day of October 1985

[SEAL]

Attest:

Attesting Officer

DONALD J. QUIGG

Commissioner of Patents and Trademarks—Designate

REEXAMINATION CERTIFICATE (786th)
United States Patent [19]

Bosker

[11] B1 4,516,937

[45] Certificate Issued Nov. 24, 1987

[54] SYSTEM FOR DENTURE SUPPORT USING A TRANSMANDIBULAR IMPLANT

[76] Inventor: Hans Bosker, Essen 14, 9751 NC Haren, Netherlands

Reexamination Request:
No. 90/000,861, Sep. 18, 1985

Reexamination Certificate for:
Patent No.: 4,516,937
Issued: May 14, 1985
Appl. No.: 556,520
Filed: Nov. 30, 1983

Certificate of Correction issued Oct. 8, 1985.

[51] Int. Cl.⁴ .................................................. A61C 8/00
[52] U.S. Cl. .................................................. 433/173
[58] Field of Search ................................. 433/173–176

[56] References Cited

U.S. PATENT DOCUMENTS

| | | | |
|---|---|---|---|
| Re. 28,841 | 6/1976 | Allgower et al. | 128/92 |
| 3,414,975 | 12/1968 | Small | 32/2 |
| 3,664,022 | 5/1972 | Small | 32/2 |
| 3,748,739 | 7/1973 | Thibert | 32/10 |
| 3,895,444 | 7/1975 | Small | 32/10 |

FOREIGN PATENT DOCUMENTS 882466  7/1951  Fed. Rep. of Germany .
770696  3/1957  United Kingdom .

OTHER PUBLICATIONS

"Use of the mandibular staple bone plate in the deformed mandible", Irwin A. Small, J Oral Surgery, vol. 37, 1979, pp. 26–30.

"The Transmandibular Implant", Hans Bosker, Sep. 1983 (English Translation).
"Metal implants and the mandibular staple bone plate", Irwin A. Small, J Oral Surgery, vol. 33, Aug. 1975, pp. 571–585.
"Mandibular staple bone plate: long-term evaluation of 250 cases", Irwin A. Small, 318 JADA, vol. 104, Mar. 1982, pp. 318–320.
"Survey of experiences with the mandibular staple bone plate", Irwin A. Small, J Oral Surgery, vol. 36, 1978, pp. 604–607.

*Primary Examiner*—Robert Peshock

[57] ABSTRACT

A system providing support on the lower jaw for a submaxillary denture wherein a base plate comprising an arcuate metal strip having an intermediate portion, the centerline of which in plan view being an arc across a subtending chord 34 mm in length and with a height of 8 or 10 mm;

a bridging means comprising hooking means for coupling means included in a submaxillary denture;
a set of posts to stand on said intermediate portion for carrying said bridging means;
a fixing means for each of said posts to fix said bridging means; and a set of cortical screws to adjoin said base plate fixedly to the lower face of the lower jaw at locations on either side of each of said posts.

Each of its parts is made up of gold 18–5 (gold of 18 carat, allowed with 5% platinum).

Auxiliary means for mounting said base plate and said posts in a lower jaw comprise a jig for drilling and tapping and a concurrent alignment means, said jig being unilaterally a replica of the face of the base plate turned to the interface with the lower jaw.

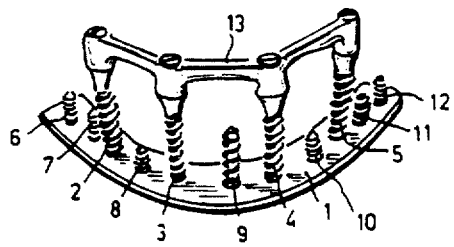

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3 are determined to be patentable as amended.

Claims 4-15, dependent on an amended claim, are determined to be patentable.

1. An apparatus providing support on the lower jaw for a submaxillary denture characterized by a base plate comprising an arcuate metal strip having an intermediate portion, the centerline of which in plan view [bring] *being* an arc across a subtending chord approximately 34 mm in length and with a height of approximately 8 to 10 mm; a bridging means comprising hooking means for coupling means included in a submaxillary denture;

a set of *at least four* posts to stand on said intermediate portion for carrying said bridging means, *said posts being independent from said base plate and adjustably positionable with respect thereto*;

a fixing means for each of said posts to fix said bridging means *and to fixedly secure said posts in place*; and a set of cortical screws to adjoin said base plate fixedly to the lower face of the lower jaw at locations on either side of each of said posts, *said posts further including means at the base ends thereof for securement to the base plate and means at the head end thereof for said fixing means.*

3. Apparatus according to claim [2] *1*, characterized in that each of said fixing means comprises a two-piece collar, said collar pieces being sequentially arranged at the head end of the post, the collar piece to be arranged firstly having an internal thread to fit the said external thread at the head end of a post, and a terminal screw to fix the collar piece to be arranged secondly.

* * * * *